United States Patent [19]

Harkins et al.

[11] Patent Number: 4,935,569
[45] Date of Patent: Jun. 19, 1990

[54] ALPHA-OLEFIN PROCESS

[75] Inventors: Alvin E. Harkins; Layne W. Summers, both of Baton Rouge, La.

[73] Assignee: Ethyl Corporation, Richmond, Va.

[21] Appl. No.: 373,247

[22] Filed: Jun. 29, 1989

[51] Int. Cl.$^5$ ............................................... C07C 2/88
[52] U.S. Cl. ..................................... 585/328; 585/522
[58] Field of Search ................................ 585/328, 522

[56] References Cited

U.S. PATENT DOCUMENTS 3,696,161 10/1972 Kobetz et al. ...................... 585/328
3,702,345 11/1972 Fernald et al. ...................... 585/328
4,314,090 2/1982 Shewbart et al. .................... 585/328
4,484,016 11/1984 Maschmeyer et al. ............... 585/328

FOREIGN PATENT DOCUMENTS 906464 3/1960 United Kingdom ................ 585/328

Primary Examiner—Curtis R. Davis
Attorney, Agent, or Firm—Joseph D. Odenweller

[57] ABSTRACT

Alpha-olfins containing about 6–14 carbon atoms are made in a dual displacement loop ethylene/tri-lower alkyl chain growth process which includes, in one closed loop, an initial ethylene/triethyl aluminum (TEA) chain growth, $C_{2-14}$ olefin separation, 2-stage ethylene displacment, $C_{2-12}$ olefin separation and recycle of residual TEA and higher olefins back to the initial ethylene/TEA chain growth. A second closed loop starts with the same ethylene/TEA chain growth product followed by $C_{4-14}$ olefin separation, $C_{4-8}$ olefin displacement on the bottoms from $C_{4-14}$ olefin separation, ethylene chain growth on the $C_{4-8}$ olefin displacement product and recycle of this ethylene displacement product back to the olefin separation stage following the initial ethylene/TEA chain growth reaction.

12 Claims, 1 Drawing Sheet

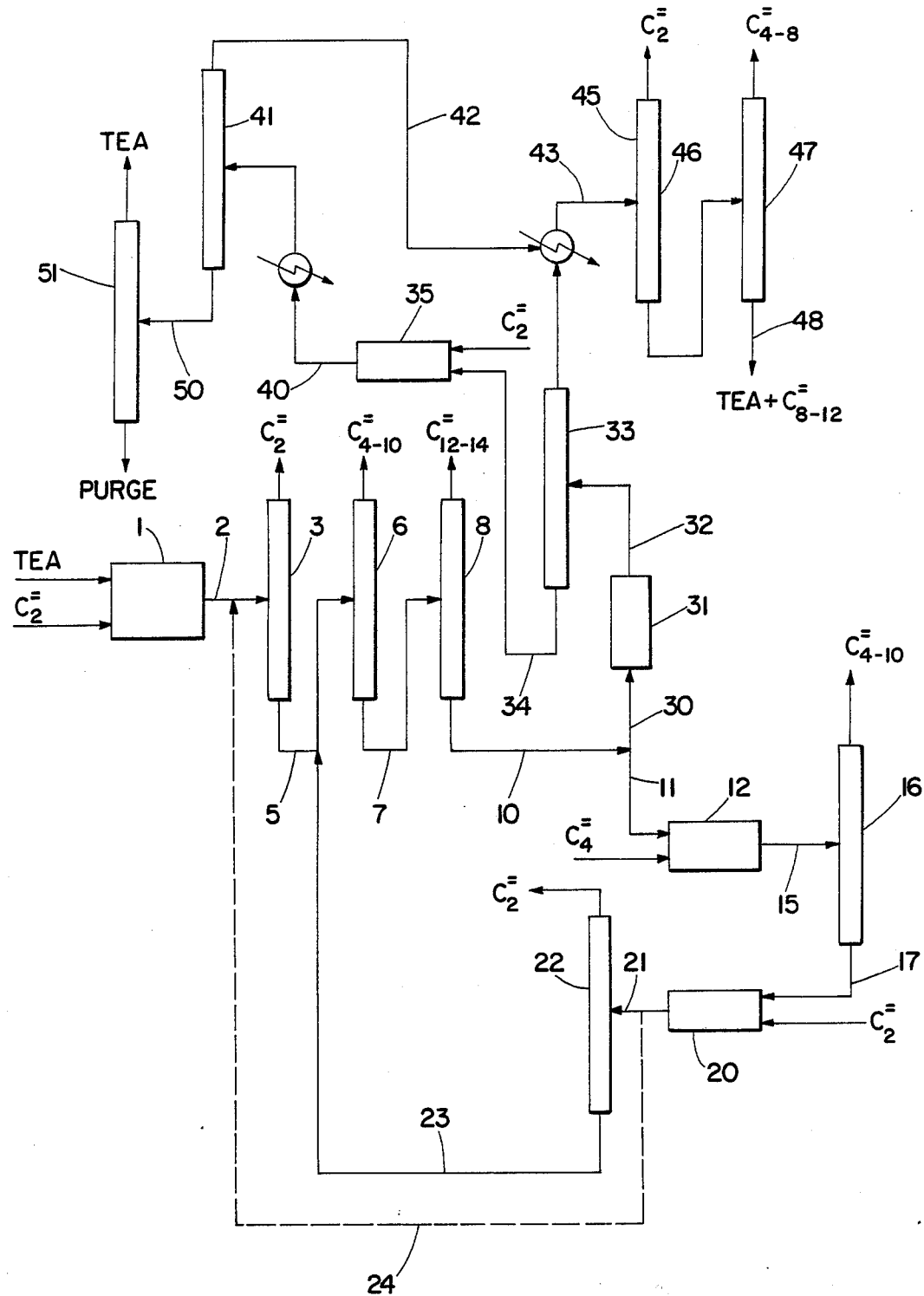

ALPHA-OLEFIN PROCESS

BACKGROUND

Alpha-olefins are made in commercial quantities by a process initially developed in the fifties by Karl Ziegler and his co-workers. The so-called Ziegler process involves the reaction of triethyl aluminum ("TEA") and ethylene at temperatures in the range of 200–500° F. and pressure in the range of 2000–5000 psig to yield a mixture of tri-$C_{2-20+}$ alkyl aluminum having a poisson alkyl distribution and $C_{2-20}$ olefins. The ethylene is flashed from the reaction mixture for recycle and the light olefins through decene-1 can be distilled from the mixed aluminum alkyls since they have a normal boiling point below the lightest aluminum alkyl (viz. TEA).

Johnson, U.S. Pat. No. 2,863,896, describes the preparation of pure aluminum alkyls using a chain growth reaction of a $C_{2-4}$ olefin (e.g. ethylene) with a low molecular weight trialkyl aluminum (e.g. TEA), dialkyl aluminum hydride or alkyl aluminum dihydride. The chain growth product contained about 2–5 percent $C_{4-20}$ olefin which could not be separated from the aluminum alkyls. The mixture was then subjected to a displacement reaction with a $C_{4-6}$ α-olefin, e.g. 1-butene, to displace mainly $C_{6-20}$ α-olefin forming tributyl aluminum. The $C_{6-20}$ α-olefins were fractionated into individual α-olefins. These individual α-olefin cuts were then reacted in a second displacement reaction with the tributyl aluminum formed in the butene displacement reaction to form pure trialkyl aluminum.

Catterall et al., U.S. Pat. No. 2,889,385, describe an ethylene chain growth reaction carried out on tributyl aluminum followed by displacement with 1-butene to regenerate tributyl aluminum and evolve $C_{4-20}$ α-olefins. This avoids the problem encountered in attempting to separate TEA from $C_{12-14}$ α-olefins which have normal boiling points close to the same temperature.

Other patents disclosing variations of the aluminum alkyl chain growth α-olefin synthesis are U.S. Pat. No. 2,906,794; U.S. Pat. No. 2,971,969; U.S. Pat. No. 3,180,881; U.S. Pat. No. 3,210,435; U.S. Pat. No. 3,227,773; U.S. Pat. No. 3,278,633; U.S. Pat. No. 3,352,940; U.S. Pat. No. 3,663,647; U.S. Pat. No. 3,789,081; U.S. Pat. No. 3,487,097; U.S. Pat. No. 4,314,090; U.S. Pat. No. 3,359,292; U.S. Pat. No. 3,384,651; U.S. Pat. No. 3,415,861; U.S. Pat. No. 3,458,594 and U.S. Pat. No. 3,358,050.

All aluminum alkyl chain growth products initially yield a mixture of higher trialkyl aluminum compounds exhibiting a poisson distribution. When ethylene and TEA are used, the mixture is mainly tri-$C_{2-20}$ alkyl aluminum compounds although a small amount of $C_{20+}$ alkyls are usually present. Ethylene displacement of this mixture yield a mixture of $C_{2-20}$ olefins. The more valuable components are the $C_{6-14}$ α-olefins. Ethylene can be recycled to chain growth and olefins above $C_{14}$ can be separated for use as diluent or can be purged. Butene is produced in fairly large amounts and cannot economically be discarded. The commercial market for butene is substantially saturated. The present invention provides a process that utilizes the butene that it produces in a closed butene displacement loop that gives high yield of the more desirable $C_{6-12}$ α-olefins.

SUMMARY

According to the present invention, $C_{6-14}$ α-olefins are produced in high yield without the need to dispose of butene by-product by conducting an initial TEA/ethylene chain growth step, distilling ethylene and $C_{4-14}$ olefins from this chain growth product and conducting at least one ethylene displacement step on the resultant distillation bottoms. This displacement forms TEA and $C_{4-20}$ α-olefin. The ethylene is separated for recycle and the $C_{4-12}$ olefins and part of the $C_{14}$ olefins are separated from the remaining $C_{14+}$ olefins and TEA. The $C_{4-14}$ α-olefins are distilled to separate 1-butene and various $C_{6-14}$ olefin fractions.

The 1-butene produced in the ethylene/TEA chain growth-ethylene displacement loop is utilized in a butene displacement loop in which ethylene/TEA chain growth product is distilled to remove ethylene and $C_{4-12}$ α-olefins and part of the $C_{14}$ olefins and a portion of the bottoms are subjected to butene displacement. Lower olefins can be distilled from the butene displacement product if desired and the butene displacement product is then subjected to ethylene chain growth to form a mixture of $C_{2-20}$ olefins and tri-$C_{2-20}$ alkyl aluminums. Ethylene is vaporized from this and the remainder is recycled to the olefin distillation zone following the initial TEA/ethylene chain growth.

DESCRIPTION OF THE DRAWING

The drawing is a schematic flow diagram of the process. Conventional equipment such as valves, pumps, heaters, coolers and the like have not been included in the drawing for the sake of improved clarity.

In the drawing, olefins are designated as $C^=$ with a subscript showing the number of carbon atoms. Hence $C_2^=$ is ethylene and $C_4^=$ is butene. A poisson distribution of trialkyl aluminum is designated by "p" followed by "tri-$C_n$ alkyl aluminum" where the subscript "n" represents the number of carbon atoms in the alkyl groups or a range of carbon atoms in the alkyl groups. For example "p tri-$C_{2-20}$ alkyl aluminum" represents a mixture of trialkyl aluminums in which the alkyl groups contain from 2 to 20 carbon atoms. The moles of each particular alkyl group in the mixture varies in a poisson distribution. Those familiar with aluminum alkyl chain growth chemistry will recognize that small amounts of alkyls having more than 20 carbon atoms may be present. Also an olefin designated as $C^=_{4-10}$ will generally contain a residual amount of $C^=_2$ and also a small amount of olefin above decene because it is not economically practical to have distillation fractions any purer than this.

DESCRIPTION OF THE PREFERRED EMBODIMENTS

A preferred embodiment of the invention is a process for making $C_{6-14}$ α-olefins said process including a butene displacement loop, said process comprising:
(A) feeding triethyl aluminum and ethylene to a first ethylene chain growth reaction zone maintained under chain growth conditions to form a first chain growth product,
(B) separating ethylene from said first chain growth product forming an ethylene-depleted first chain growth product,
(C) distilling said ethylene-depleted first chain growth product whereby $C_{4-14}$ α-olefins are distilled from said ethylene-depleted first chain growth product leaving a bottoms stream comprising mainly poisson distributed tri-$C_{2-20+}$ alkyl aluminum and $C_{14+}$ α-olefins, (D) conveying at least part of said bottoms stream to a $C_{4-8}$ olefin displacement zone maintained under displacement conditions and feeding $C_{4-8}$ olefin to said displacement zone thereby forming a $C_{4-8}$ olefin displaced product comprising mainly tri-$C_{4-8}$ alkyl aluminum, ethylene and $C_{4-20+}$ α-olefins, (E) conveying said $C_{4-8}$ olefin displaced product to a second ethylene chain growth reaction zone maintained under chain growth conditions and feeding ethylene to said second ethylene chain growth zone thereby forming a second chain growth product comprising mainly ethylene, $C_{4-20}$ α-olefins and poisson distributed tri-$C_{4-20}$ alkyl aluminums, (F) vaporizing ethylene from said second chain growth product forming an ethylene-depleted second chain growth product, (G) distilling said ethylene-depleted second chain growth product whereby $C_{4-14}$ α-olefins are distilled from said ethylene-depleted second chain growth product leaving a bottoms stream as defined in step (C).

A still further preferred embodiment of the invention includes both a $C_{4-8}$ olefin displacement loop and an ethylene displacement loop. In this embodiment any $C_{4-8}$ olefin formed in either loop can be used as feed olefin to the $C_{4-8}$ olefin displacement reactor. This dual loop process includes steps (A) through (G) as stated above and also includes the additional steps of:

(H) conveying a portion of said bottoms stream from step (C) to an ethylene displacement zone maintained under displacement conditions and feeding ethylene to said ethylene displacement zone thereby forming an ethylene displaced product comprising mainly triethyl aluminum, ethylene and $C_{4-20+}$ α-olefins, (I) distilling $C_{2-12}$ α-olefins from said ethylene displaced product forming a bottoms liquid comprising mainly triethyl aluminum and $C_{14+}$ α-olefins, (J) recycling said bottoms liquid to said first ethylene chain growth reaction zone.

A most preferred embodiment of the dual loop process includes steps (A) through (G) as set forth above and also the additional steps of:

(H) conveying a portion of said bottoms stream from step (C) to a first ethylene displacement zone maintained under displacement conditions and feeding ethylene to said first ethylene displacement zone in an amount which displaces about 75–95 mole percent of the $C_{4-20}$ alkyl groups bonded to aluminum thereby forming a partially displaced product comprising mainly ethylene, tri-$C_{2-20}$ alkyl aluminum and $C_{4-20}$ α-olefins, (I) distilling ethylene and $C_{4-12}$ α-olefin from said partially-displaced product forming a bottoms fluid comprising mainly tri-$C_{2-20}$ alkyl aluminum and $C_{14-20}$ α-olefins, (J) conveying said bottoms fluid to a second ethylene displacement zone maintained under displacement conditions and feeding ethylene to said second ethylene displacement zone in an amount sufficient to complete the ethylene displacement reaction forming a second ethylene-displaced product comprising mainly ethylene, $C_{4-20}$ α-olefins and triethyl aluminum, (K) distilling said second ethylene displaced product to separate mainly ethylene and $C_{4-12}$ α-olefins leaving a bottoms stream comprising mainly $C_{14+}$ olefins and triethyl aluminum.

The process is best described by reference to the drawing. The drawing is a schematic flow diagram of a preferred embodiment of the process including ethylene chain growth, a 2-stage ethylene displacement loop and a butene displacement-ethylene displacement loop. In the drawing ethylene ("$C_2=$") and triethyl aluminum ("TEA") are fed to first ethylene chain growth reactor 1 in a mole ratio of about 4–10/1. Chain growth reactor 1 is maintained under chain growth conditions. These are a temperature in the range of about 200–500° F., more preferably 225–350° F., and a pressure of about 2000–5000 psig, more preferably 2000–3500 psig. Residence time of ethylene and TEA in chain growth reactor 1 should be long enough to increase the chain length of the alkyls bonded to aluminum to a mole average chain length of about 6–12 carbon atoms. Depending on temperature and pressure, a residence time on the order of 15 minutes to about 1 hour is usually satisfactory.

The first chain growth product formed in chain growth reactor 1 is conveyed via conduit 2 into vapor-liquid separator 3 which is at a lower pressure than chain growth reactor 1 causing most of the residual ethylene in the first chain growth product to vaporize and be removed overhead. All ethylene streams separated in the process are recycled to one of the ethylene chain growth reactors or ethylene displacement reactors which consume all the separated ethylene.

The ethylene-depleted first chain growth product from separator 3 is transferred via conduit 5 to distillation unit 6 which serves to distill out $C_{4-10}$ olefins. Distillation unit 6 is shown as a single unit but is preferably a series of 2-3 separation units each in sequence at a lower pressure than the preceding unit.

The bottoms from distillation unit 6 are transferred via conduit 7 to a mid-point in vacuum rectification column 8. Column 8 is operated in a range of about 5–30 torr with its reboiler adjusted to maintain reflux conditions in the rectification zone above the mid-point in a temperature range of about 200–250° F. Under these conditions, 1-dodecene together with some 1-decene and 1-tetradecene are distilled overhead with little contamination by TEA which has about the same normal boiling point.

The $C_{4-14}$ olefins removed are transferred to a distillation area (not shown) where they are combined with olefins recovered from other sections of the overall process and fractionated to recover butene for feed to the butene displacement unit to be described later and to form olefin fractions, e.g. 1-octene, 1-decene, 1-dodecene, suitable for sales. In an optional embodiment other $C_{4-8}$ α-olefins can be combined and used as feed to the butene displacement reactor in which case it should be referred to as a $C_{4-8}$ olefin displacement reactor. Generally the olefin in excess over demand in the overall process is 1-butene. Linear low density polyethylene (LLDPE) provide a market for all 1-hexene. Excess 1-octene can be combined with the 1-butene as feed to the $C_{4-8}$ olefin displacement reactor. However, in a most preferred embodiment the $C_{4-8}$ olefin is mainly, i.e. 60–100 weight percent and preferably 75–100 weight percent and most preferably 90–100 weight percent, 1-butene.

The bottoms stream from vacuum column 8 comprises mainly poisson distributed tri-$C_{2-20+}$ alkyl aluminums and $C_{14+}$ olefins. A portion of this stream depending on the amount of 1-butene available but generally about 75–95 weight percent is conveyed via conduits 10 and 11 to butene displacement zone 12.

Butene displacement zone 12 is maintained under displacement conditions. This requires a temperature in the range of about 500–750° F. and a pressure of about 1000–2000 psig. In addition, 1-butene is pumped into zone 12 in an amount sufficient to provide about 3.5–10 moles of 1-butene per mole of aluminum alkyl. The displacement reaction is fast. An average residence time of about 0.1 to 1 second is usually adequate. This results in butene displacement of most of the alkyl groups bonded to aluminum forming a butene-displaced product comprising mainly tributyl aluminum, residual tri-$C_{2-20}$ alkyl aluminum, ethylene and $C_{4-20+}$ α-olefins.

The butene-displaced product is transferred via conduit 15 to distillation unit 16 which functions to flash off ethylene and distill out $C_{4-10}$ α-olefins. The ethylene is recycled to chain growth and the $C_{4-10}$ olefins are transferred to the distillation area mentioned earlier for separation into various fractions.

The bottoms stream from distillation unit 16 is transferred via conduit 17 to second ethylene chain growth reactor 20 maintained under chain growth conditions. These conditions are the same as in the first ethylene chain growth reaction zone, i.e. 200–500° F., 2000–5000 psig, residence time 15 minutes to 1 hour. Ethylene is fed to second ethylene chain growth reactor 20 in an amount sufficient to increase the average chain length of the alkyls to about 6–8 carbon atoms. This usually requires about 3–6 moles of ethylene per mole of aluminum alkyl. This results in a second chain growth product comprising mainly ethylene, $C_{4-20}$ α-olefins and tri-$C_{4-20}$ alkyl aluminum.

The second chain growth product is conveyed via conduit 21 to ethylene separator 22 wherein ethylene is flashed off at a lower pressure. The ethylene-depleted liquid phase from separator 22 comprises mainly $C_{4-20}$ α-olefins and tri-$C_{2-20}$ alkyl aluminums and is conveyed via conduit 23 back to conduit 5 leading to distillation unit 6, thus completing the butene loop. In an alternate arrangement, second chain growth product from reactor 20 is transferred from conduit 21 via conduit 24 (shown as dashed line) to vapor-liquid separator 3 wherein ethylene separation is performed.

It was previously described that in the most preferred embodiment only part of the bottoms stream from vacuum column 8 was conveyed to butene displacement zone 12. The remainder is subjected to an ethylene displacement loop. In this embodiment, the remaining portion of the bottoms stream from rectification column 8 is conveyed via conduit 30 to ethylene displacement zone 31 maintained under ethylene displacement conditions. These are about 450–700° F. at 200–400 psig with an average residence time of 0.1–5 seconds. Ethylene is also pumped into displacement zone 31 in an amount sufficient to displace most of the non-ethyl alkyl groups bonded to aluminum. This requires about 5–10 moles of ethylene per mole of aluminum alkyl. This results in an ethylene displaced product comprising mainly TEA, ethylene and $C_{4-20+}$ α-olefins. In one embodiment, this stream is subject to a flash vaporization to remove most of the ethylene and the liquid phase is further distilled to remove $C_{4-12}$ α-olefins and the distillation bottoms are recycled to the first ethylene chain growth reaction zone.

The more preferred ethylene displacement loop uses two ethylene displacement operations. In this embodiment, ethylene displacement zone 31 is referred to as first ethylene displacement zone 31. The amount of ethylene pumped to displacement zone 31 is adjusted such that under the displacement conditions used, only about 75–95 mole percent of the aluminum alkyls form TEA resulting in a partially displaced product comprising mainly ethylene, tri-$C_{2-20}$ alkyl aluminum and $C_{4-20}$ α-olefins.

The partially displaced product is conveyed via conduit 32 to distillation unit 33 which functions to distill out $C_{2-12}$ olefins and part of the TEA forming a bottoms fluid comprising mainly tri-$C_{2-20}$ alkyl aluminum and $C_{14-20}$ olefins. This bottoms fluid is conveyed via conduit 34 to second ethylene displacement unit 35 maintained under ethylene displacement conditions. Ethylene is fed to second ethylene displacement unit 35 in an amount sufficient to complete the displacement of non-ethyl alkyl groups bonded to aluminums forming a second ethylene-displaced product comprising mainly ethylene, $C_{4-20+}$ α-olefins and TEA.

This second ethylene-displaced product is transferred via conduit 40 to distillation unit 41 which functions to distill ethylene, $C_{4-12}$ α-olefin and part of the remaining TEA overhead. This distillate is combined via conduit 42 with the overhead stream from distillation unit 33 and the combined stream 43 is subjected to flash vaporization in flash unit 45 to remove ethylene. The ethylene-depleted bottoms mixture from flash unit 45 is conveyed via conduit 46 to distillation unit 47 wherein $C_{4-6}$ α-olefins are distilled overhead and the bottoms stream comprising TEA and residual $C_{8-12}$ olefins is conveyed via conduit 48 back to first ethylene chain growth reaction zone as part of the TEA feed. This completes the ethylene displacement loop.

To regress somewhat, the bottoms from distillation unit 41 are conducted via conduit 50 to a mid-point in vacuum rectification column 51 maintained at 15–30 torr. In column 51, TEA is distilled overhead for recycle and the bottoms stream comprising mainly heavy $C_{14+}$ olefins and heavy aluminum alkyls is conveyed to a disposal area as a purge stream.

We claim:
1. A process for making $C_{6-14}$ α-olefins, said process including a butene displacement loop, said process comprising:
(A) feeding triethyl aluminum and ethylene to a first ethylene chain growth reaction zone maintained under chain growth conditions to form a first chain growth product,
(B) separating ethylene from said first chain growth product forming an ethylene-depleted first chain growth product,
(C) distilling said ethylene-depleted first chain growth product whereby $C_{4-14}$ α-olefins are distilled from said ethylene-depleted first chain growth product leaving a bottoms stream comprising mainly poisson distributed tri-$C_{2-20+}$ alkyl aluminum and $C_{14+}$ α-olefins,
(D) conveying at least part of said bottoms stream to a $C_{4-8}$ olefin displacement zone maintained under displacement conditions and feeding $C_{4-8}$ olefin to said $C_{4-8}$ olefin displacement zone thereby forming a $C_{4-8}$ olefin displaced product comprising mainly tri-$C_{4-8}$ alkyl aluminum, ethylene and $C_{4-20+}$ α-olefins,
(E) conveying said $C_{4-8}$ olefin displaced product to a second ethylene chain growth reaction zone maintained under chain growth conditions and feeding ethylene to said second ethylene chain growth zone thereby forming a second chain growth product com- prising mainly ethylene, $C_{4-20}$ α-olefins and poisson distributed tri-$C_{4-20}$ alkyl aluminums, (F) vaporizing ethylene from said second chain growth product forming an ethylene-depleted second chain growth product, (G) distilling said ethylene-depleted second chain growth product whereby $C_{4-14}$ α-olefins are distilled from said ethylene-depleted second chain growth product leaving a bottoms stream as defined in step (C).

2. A process of claim 1 wherein said $C_{4-8}$ olefin in step D is mainly 1-butene which forms a butene displaced product.

3. A process of claim 2 wherein said butene-displaced product from step (D) is distilled to separate mainly $C_{4-10}$ α-olefins and the bottoms from this distillation are conveyed to said second ethylene displacement zone in step (E).

4. A process of claim 1 further defined to include an ethylene displacement loop, said process comprising:

(H) conveying a portion of said bottoms stream from step (C) to an ethylene displacement zone maintained under displacement conditions and feeding ethylene to said ethylene displacement zone thereby forming an ethylene-displaced product comprising mainly triethyl aluminum, ethylene and $C_{4-20+}$ α-olefins, (I) distilling $C_{2-12}$ α-olefins from said ethylene-displaced product forming a bottoms liquid comprising mainly triethyl aluminum and $C_{14+}$ α-olefins, (J) recycling said bottoms liquid to said first ethylene chain growth reaction zone.

5. A process of claim 4 wherein said $C_{4-8}$ olefin in step D is mainly 1-butene which forms a butene-displaced product.

6. A process of claim 1 further defined to include an ethylene displacement loop, said process comprising:

(H) conveying a portion of said bottoms stream from step (C) to a first ethylene displacement zone maintained under displacement conditions and feeding ethylene to said first ethylene displacement zone in an amount which displaces about 75-95 mole percent of the $C_{4-20}$ alkyl groups bonded to aluminum thereby forming a partially-displaced product comprising mainly ethylene, tri-$C_{2-20}$ alkyl aluminum and $C_{4-20}$ α-olefins, (I) distilling ethylene, triethyl aluminum and $C_{4-12}$ α-olefin from said partially-displaced product forming a bottoms fluid comprising mainly tri-$C_{2-20}$ alkyl aluminum and $C_{14-20}$ α-olefins, (J) conveying said bottoms fluid to a second ethylene displacement zone maintained under displacement conditions and feeding ethylene to said second ethylene displacement zone in an amount sufficient to complete the ethylene displacement reaction forming a second ethylene-displaced product comprising mainly ethylene, $C_{4-20}$ α-olefins and triethyl aluminum, (K) distilling said second ethylene displaced product to separate mainly ethylene and $C_{4-12}$ α-olefins leaving a bottoms mixture comprising mainly $C_{14+}$ *olefins and triethyl aluminum.*

7. A process of claim 6 wherein said $C_{4-8}$ olefin in step D is mainly 1-butene which forms a butene-displaced product.

8. A process of claim 7 wherein said bottoms mixture is distilled to recover triethyl aluminum in the distillate.

9. A process of claim 7 wherein said ethylene and $C_{4-12}$ α-olefins distilled in step (I) and/or (K) are again distilled to separate ethylene and $C_{4-12}$ α-olefin leaving a bottoms product comprising mainly $C_{8-12}$ olefins and TEA.

10. A process of claim 9 wherein said bottoms product is recycled to said first ethylene chain growth reaction zone in step (A).

11. A dual loop α-olefin process comprising an initial ethylene/triethyl aluminum chain growth reaction zone wherein ethylene and triethyl aluminum react under chain growth conditions to increase the chain length of alkyls bonded to aluminum resulting in an ethylene chain growth product, a distillation zone wherein $C_{2-14}$ olefins are distilled from said ethylene chain growth product forming an olefin-depleted bottoms stream, conducting 10-90 weight percent of said olefin-depleted bottoms stream to a butene displacement loop, said butene displacement loop comprising a butene displacement reaction zone wherein butene is reacted with said portion of said olefin-depleted bottoms stream under displacement conditions forming a butene-displaced product, subjecting said butene-displaced product to an ethylene chain growth reaction under chain growth conditions to form a mixture comprising tri-$C_{2-20}$ alkyl aluminum and $C_{4-20}$ α-olefins and conducting said mixture to said distillation zone to complete the butene displacement loop, conducting the remaining portion of said olefin-depleted bottoms stream to an ethylene displacement loop, said ethylene displacement loop comprising at least one ethylene displacement reaction zone wherein ethylene is reacted with said remaining portion of said olefin-depleted bottoms stream under displacement conditions forming an ethylene-displaced product, separating ethylene and $C_{4-12}$ α-olefins from said ethylene-displaced product leaving a bottoms product and recycling said bottoms product to said initial ethylene/triethyl aluminum chain growth reaction to complete the ethylene displacement loop.

12. A process of claim 11 wherein $C_{4-10}$ olefins are distilled from said butene-displaced product prior to subjecting said butene-displaced product to said ethylene chain growth.

* * * * *